US007927297B2

(12) United States Patent
Češko et al.

(10) Patent No.: US 7,927,297 B2
(45) Date of Patent: Apr. 19, 2011

(54) THERAPEUTIC TREATMENT APPARATUS AND METHOD

(75) Inventors: Sandi Češko, Zagorje ob Savi (SI); Toni Kancilja, Ljubljana (SI); Stef Harley, Ljubljana (SI)

(73) Assignee: Studio Moderna SA, Lugano (CH)

( * ) Notice: Subject to any disclaimer, the term of this patent is extended or adjusted under 35 U.S.C. 154(b) by 106 days.

(21) Appl. No.: 11/801,985

(22) Filed: May 11, 2007

(65) Prior Publication Data

US 2007/0208288 A1 Sep. 6, 2007

Related U.S. Application Data

(62) Division of application No. 10/383,854, filed on Mar. 7, 2003, now Pat. No. 7,247,145.

(60) Provisional application No. 60/410,365, filed on Sep. 11, 2002.

(51) Int. Cl.

| | |
|---|---|
| ***A61F 5/00*** | (2006.01) |
| ***A41F 1/00*** | (2006.01) |
| ***A44B 1/04*** | (2006.01) |
| ***A43C 11/00*** | (2006.01) |
| ***A61G 15/00*** | (2006.01) |
| ***A41D 1/04*** | (2006.01) |
| ***A61B 17/00*** | (2006.01) |

(52) U.S. Cl. ............ 602/19; 24/614; 128/845; 606/201; 606/203; 2/92

(58) Field of Classification Search ................ 602/6, 18, 602/19, 202, 61; 128/907, 95.1, 99.1, 105.1, 128/106.1, 107.1, 845; 2/4, 92; 24/195, 24/606, 625, 637; 606/201, 20 D
See application file for complete search history.

(56) References Cited

U.S. PATENT DOCUMENTS

| | | | |
|---|---|---|---|
| 2,447,698 | A | 8/1948 | Harberer |
| 3,605,731 | A | 9/1971 | Tigges |

(Continued)

FOREIGN PATENT DOCUMENTS

| | | |
|---|---|---|
| DE | 120697 | 5/1901 |

(Continued)

OTHER PUBLICATIONS

KOSMODISK Brochure (undated, but understood by Applicants to have been published after Apr. 1991).

*Primary Examiner* — Patricia M Bianco
*Assistant Examiner* — Tarla R Patel
(74) *Attorney, Agent, or Firm* — Mitchell P. Brook; Luce, Forward, Hamilton & Scripps LLP

(57) ABSTRACT

An improved treatment apparatus and method of using in which the device has plural protruding contact elements, each preferably having an undulating contact surface with one or more peaks. In one preferred embodiment, a plurality of contact elements are positioned spaced apart from one another in columns. In another device an elongated single column is provided. Mounting brackets are provided that enable a user to position the device easily and to adjust mounting straps and/or belts to a particular body shape. In one example, the device may include bracket apertures into which mounting brackets can be positioned. In another aspect of the invention, adjustable buckles and/or binders are provided can be used to adjust the length of the straps and secure the device to the wearer in use.

20 Claims, 15 Drawing Sheets

U.S. PATENT DOCUMENTS

| | | | | |
|---|---|---|---|---|
| 4,230,099 | A | 10/1980 | Richardson | |
| 4,411,258 | A | 10/1983 | Pujals, Jr. | |
| 4,421,110 | A | 12/1983 | DeLisle | |
| 4,622,957 | A | 11/1986 | Curlee | |
| 4,680,812 | A * | 7/1987 | Weigl | 2/467 |
| 4,716,898 | A | 1/1988 | Chauve et al. | |
| 4,760,842 | A | 8/1988 | Holmes | |
| 5,007,633 | A | 4/1991 | Lemire | |
| 5,035,017 | A | 7/1991 | Komuro | |
| 5,048,509 | A | 9/1991 | Grundei et al. | |
| 5,103,808 | A | 4/1992 | Iams et al. | |
| 5,120,288 | A | 6/1992 | Sinaki | |
| 5,140,995 | A | 8/1992 | Uhl | |
| 5,158,073 | A | 10/1992 | Bukowski | |
| 5,267,947 | A | 12/1993 | James et al. | |
| 5,275,581 | A | 1/1994 | Bender | |
| 5,290,307 | A | 3/1994 | Choy | |
| 5,312,350 | A | 5/1994 | Jacobs | |
| 5,328,447 | A | 7/1994 | Kapounek et al. | |
| 5,352,188 | A | 10/1994 | Vitko | |
| 5,410,755 | A | 5/1995 | Obujen | |
| 5,437,614 | A | 8/1995 | Grim | |
| 5,498,233 | A | 3/1996 | Stojanovic | |
| 5,797,955 | A | 8/1998 | Walters | |
| 5,843,009 | A | 12/1998 | Stojanovic | |
| 6,071,257 | A * | 6/2000 | Stojanovic | 602/19 |
| D435,109 | S | 12/2000 | Stojanovic | |
| 6,189,348 | B1 | 2/2001 | Huang | |
| 6,389,653 | B1 | 5/2002 | Matoba | |
| 6,571,434 | B2 * | 6/2003 | Ortiz | 24/615 |
| 6,700,031 | B1 | 3/2004 | Hahn | |
| D499,846 | S | 12/2004 | Cesko | |

FOREIGN PATENT DOCUMENTS

| | | | |
|---|---|---|---|
| DE | 2128410 | | 12/1972 |
| DE | 2334500 | | 1/1975 |
| DE | 2506647 | | 10/1976 |
| DE | 3525521 | A1 | 1/1987 |
| FR | 2187284 | | 1/1974 |
| GB | 2193429 | A | 2/1998 |
| JP | 09-149929 | | 6/1997 |
| JP | 2001-070398 | | 3/2001 |
| SU | 1120997 | A | 10/1984 |
| WO | WO 86/05091 | | 9/1986 |

* cited by examiner

THERAPEUTIC TREATMENT APPARATUS AND METHOD

The present application is a divisional application of U.S. application Ser. No. 10/383,854, filed on Mar. 7, 2003, which claims the benefit of U.S. provisional application No. 60/410,365, filed Sep. 11, 2002, the disclosures of which are hereby incorporated by reference.

FIELD OF THE INVENTION

The present invention relates to an therapeutic treatment apparatus that can be worn by a person and a method of using it.

BACKGROUND OF THE INVENTION

Various types of devices for treatment of a person's musculature, joints or spinal system are known. Some of those devices take the form of back braces for straightening the spinal column. Others are for applying pressure in order to create a heating or massaging type of effect. Some such devices are mechanized so as to apply a vibratory pressure or active heating. Others apply pressure passively.

It is known that massaging or using devices applied externally to the body can impart pressure and otherwise have a soothing and/or pain relief effect. One typical pressure application device is illustrated in German Disclosure No. 2,128,410. Such a device provides a backbone to which discreet brackets are mounted. Each of the brackets, has two support surfaces for applying pressure or support to the back of the person wearing the device. Such devices suffer disadvantages of being rigid and thereby failing to contour to the shape of the body of the wearer. Furthermore, they typically lack flexibility for easily increasing or decreasing the size of the area for application of pressure or other treatment. They also are composed of multiple parts.

Another example of a treatment device can be found in U.S. Pat. No. 6,017,257, which relates to a device having one or more linkable segments, each segment including plural contact elements having one or more peaks. In use, the contact elements can be situated in contact with or in proximity to the wearer.

Another type of pressure application device is illustrated in U.S. Pat. No. 4,716,898. In that device, a "stimulating member" for applying pressure to acupuncture points is rigidly connected to a belt device for keeping the member pressed onto a desired portion of a body.

SUMMARY OF THE INVENTION

The present invention provides an improved treatment apparatus and method of using in which the device has plural protruding contact elements, each preferably having an undulating contact surface with one or more peaks. In one preferred embodiment, a plurality of contact elements are positioned spaced apart from one another in columns. Two or more columns are positioned side-by-side. In a preferred construction, a unitary structure is formed in which each of the contact elements are positioned on a single mounting surface. Preferably the arrangement of elements is molded in a single component, each of the contact elements protruding from this integral arrangement.

Mounting brackets are provided that enable a user to position the device easily and to adjust mounting straps and/or belts to her or his particular body shape. This has an advantage of enhancing the flexibility of the design and enhancing wearer comfort and therapeutic effectiveness. In one example, the device may include bracket apertures into which mounting brackets can be positioned. The straps in this embodiment are secured to the device using the brackets, or to other mounting structures. Adjustable buckles and/or binders can be used to adjust the length of the straps and secure the device to the wearer in use. The use of removable mounting brackets affords the advantages of ease of maintenance and cleaning as well.

In another preferred embodiment, a single column of spaced apart contact elements is provided. One or more slidable mounting brackets are positioned on the device, whereby they can be slid up or down to an appropriate position for the wearer. One or more stops may be positioned at respective top or bottom ends to impede the bracket from sliding off. Alternatively fixed strap mounts may be used, or a combination of movable brackets and fixed brackets mounts can be used. Straps in this embodiment are secured to the device using the brackets, or by using mounting structures. Adjustable buckles can be used to adjust the length of the straps and secure the device to the wearer in use. Preferably the buckles allow for attachment of mounting straps without sewing or other form of attachment, and are easily operated by a user for fastening and unfastening.

In operation, the device is applied such that the respective surfaces of the contact elements can contact the body of the wearer. The buckles, straps, and mounting brackets are adjusted as desired, both for comfort and therapeutic effect.

In one embodiment, a carrying bag is provided, in which one or more of the therapeutic treatment devices can be positioned. An advantage of this arrangement is that the device is hidden from view, advantageous for wearing in public, or in a means of transport such as a train or automobile.

In addition, the device preferably is formed of a flexible material, such as a molded polymer or other flexible material. In this way, flexing can assist with maximizing the contact with the wearer, such as by contouring to the shape of the wearer's body and thereby enhancing the surface area that comes into contact with the wearer. Multiple devices can be linked together.

The treatment apparatus may be worn while the wearer is awake or asleep. As the wearer moves, the device can impart a massaging, warming and/or stimulating effect to the covered area. Likewise, the device may apply pressure to the area contacted and through massaging can assist blood circulation as well.

The treatment apparatus may be applied to the back, spine, or alternatively to joints, such as an elbow or knee, or for application horizontally across the back, such as to the lower back. Straps can be used in order to affix the apparatus to the body and thereby create a contact pressure or allow the apparatus to be worn when moving about.

BRIEF DESCRIPTION OF THE DRAWINGS

The above and other objects and advantages of the invention will be apparent upon consideration of the following detailed description, taken in conjunction with the accompanying drawings in which like reference characters refer to like parts throughout, and in which.

DETAILED DESCRIPTION OF THE INVENTION

Figure 1:
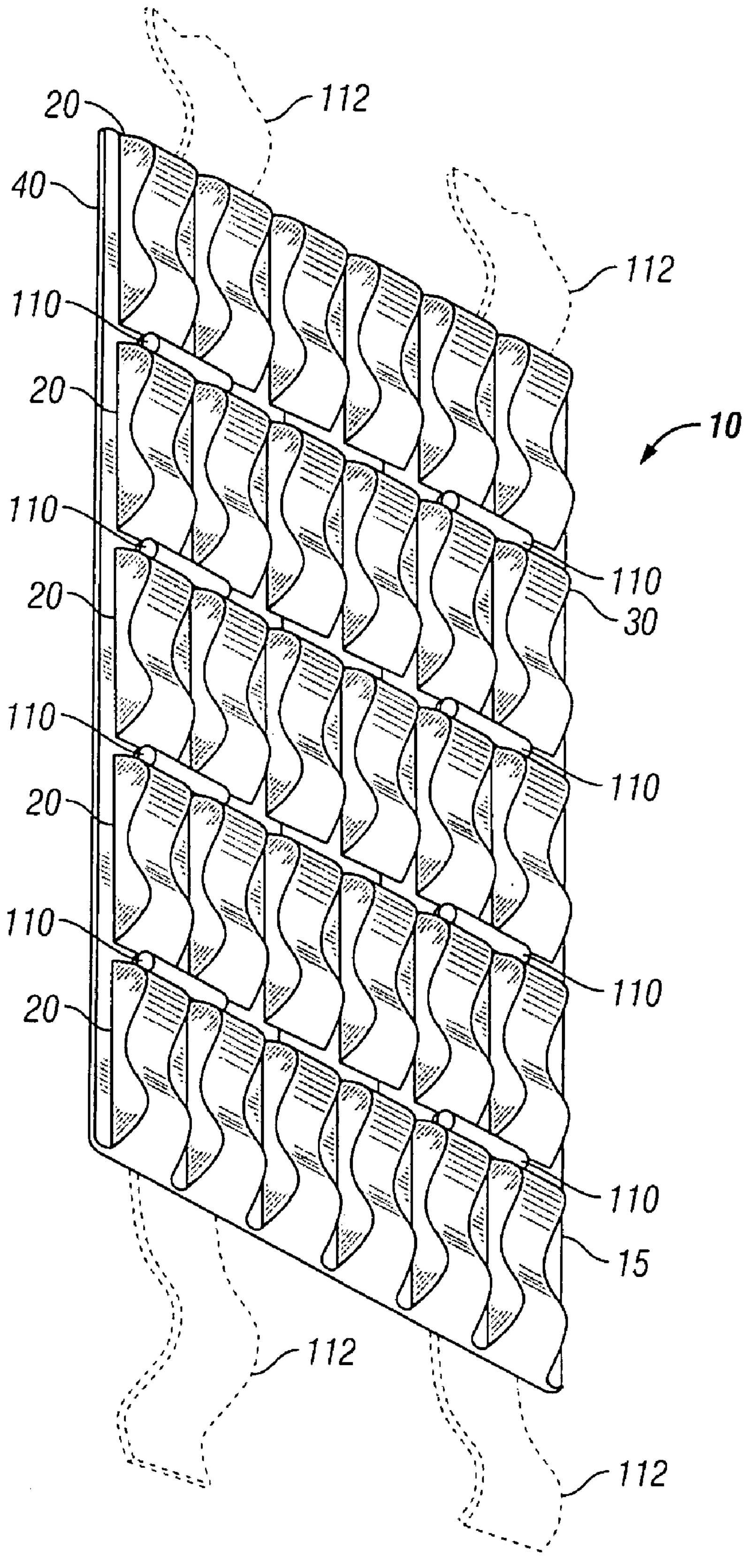
FIG. 1 illustrates a perspective view of a multi-column embodiment of the therapeutic treatment apparatus in accordance with the present invention.
Figure 2:
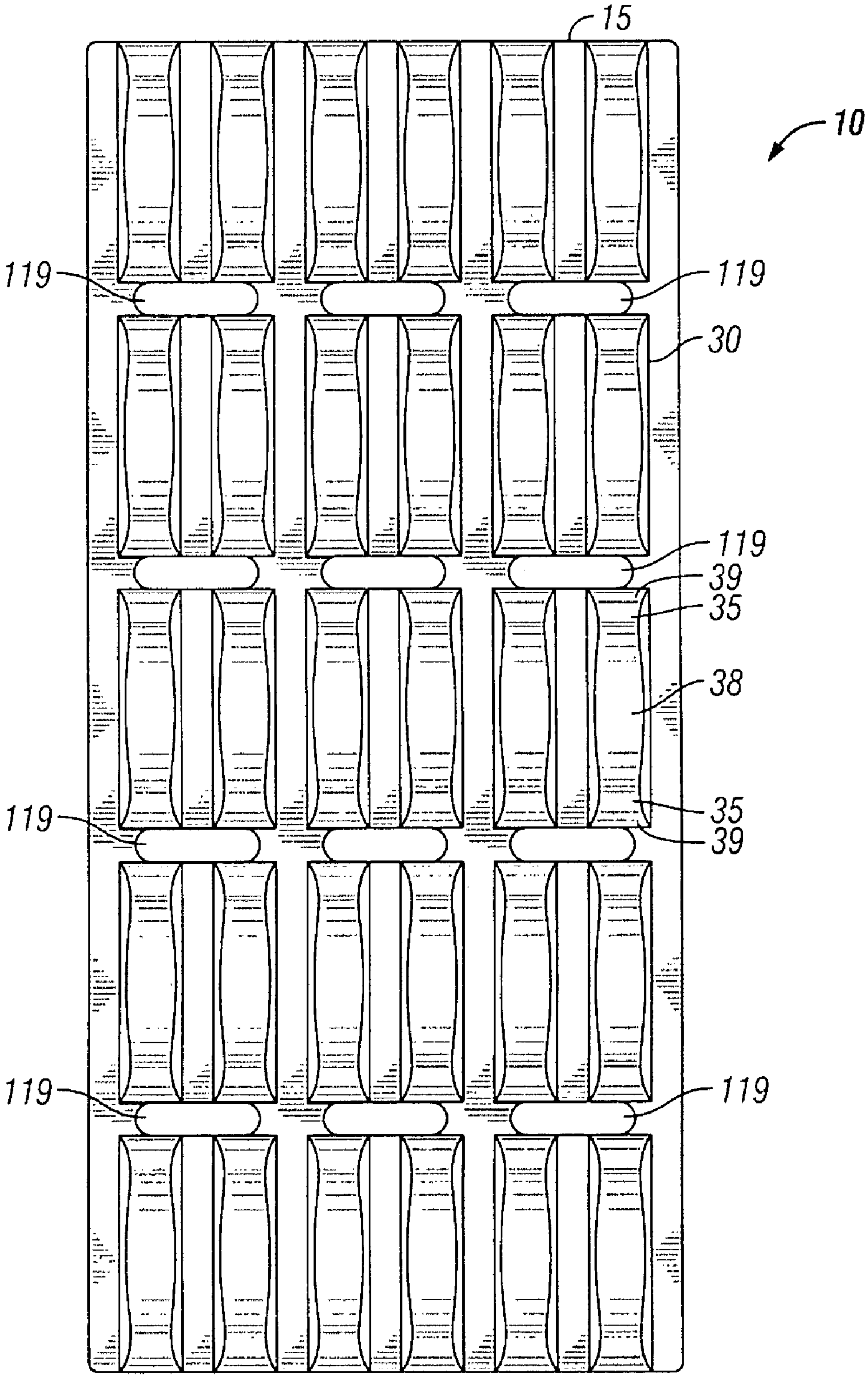
FIG. 2 illustrates a front view of a multi-column embodiment of the therapeutic treatment apparatus in accordance with the present invention.
Figure 3:
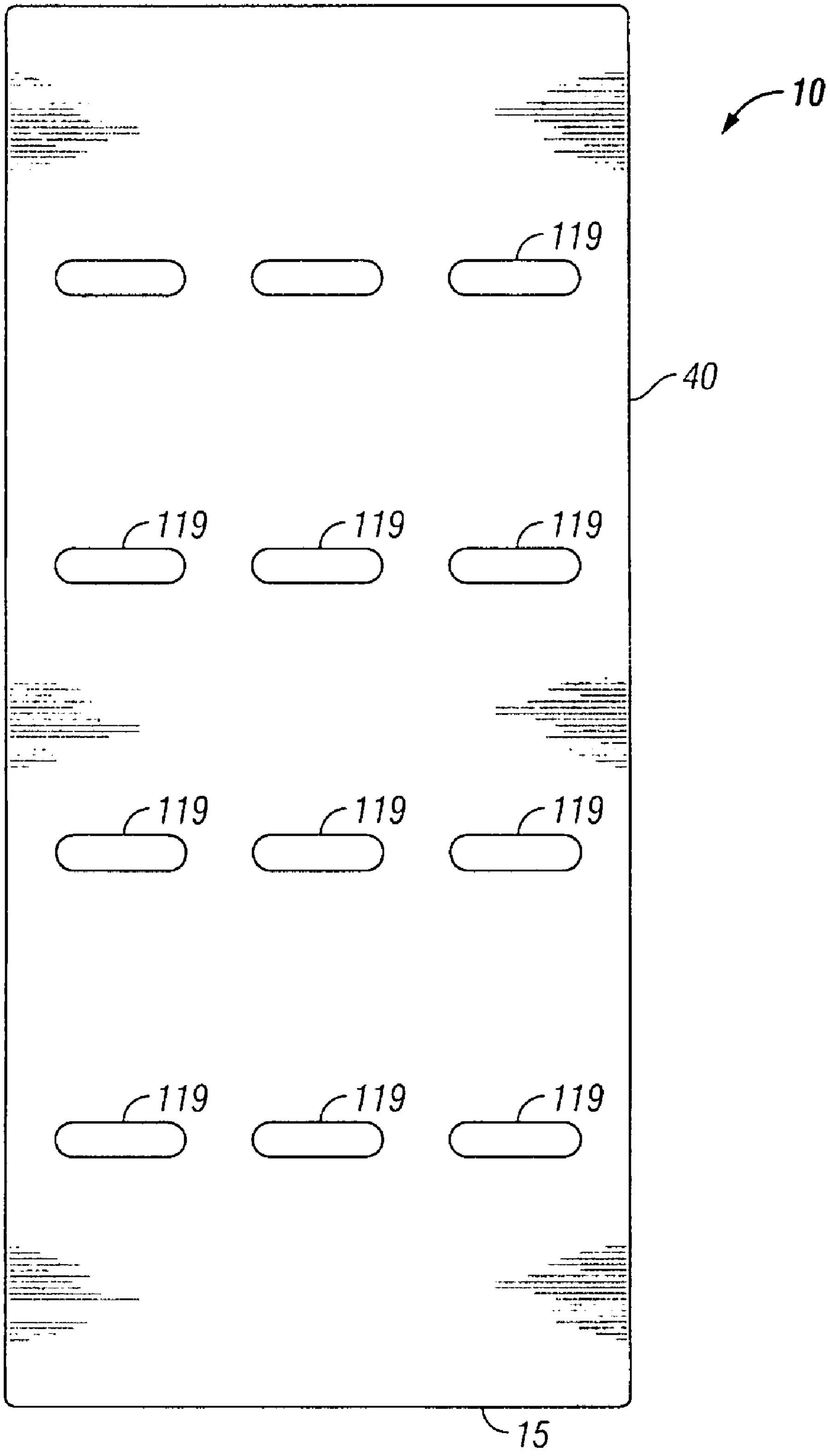
FIG. 3 illustrates a back view of a multi-column embodiment of the therapeutic treatment apparatus in accordance with the present invention.
Figure 4:
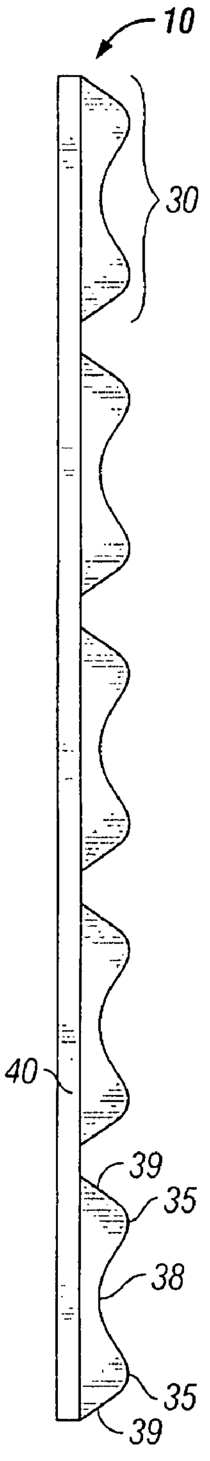
FIG. 4 illustrates a top view of a multi-column embodiment of the therapeutic treatment apparatus in accordance with the present invention.
Figure 5:
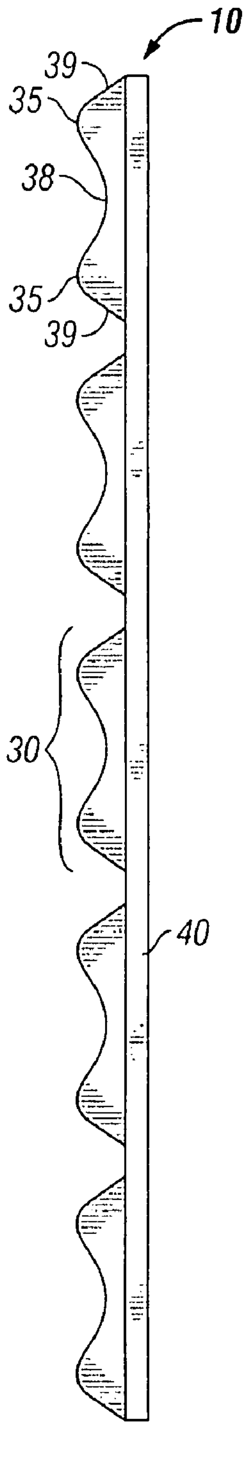
FIG. 5 illustrates a bottom view of a multi-column embodiment of the therapeutic treatment apparatus in accordance with the present invention.
Figure 6:
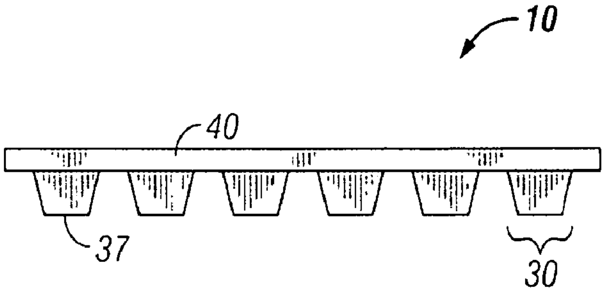
FIG. 6 illustrates a first side view of a multi-column embodiment of the therapeutic treatment apparatus in accordance with the present invention.
Figure 7:
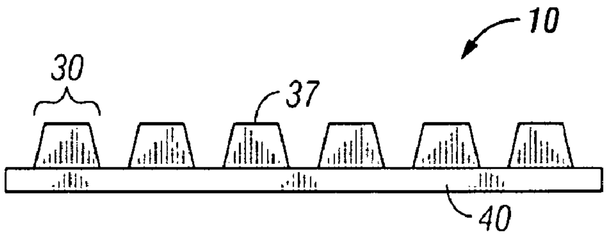
FIG. 7 illustrates a second side view of a multi-column embodiment of the therapeutic treatment apparatus in accordance with the present invention.

In the following paragraphs, the present invention will be described in detail and by way of example with reference to the figures. Throughout this description, the preferred embodiments and examples shown should be considered as exemplars, rather than as limitations of the present invention. As used herein, the "present invention" refers to any one of the embodiments described herein, and any equivalents. Furthermore, reference to various feature(s) of the "present invention" throughout this document does not mean that all claimed embodiments must include the referenced feature(s).

FIGS. 1-8 illustrate a side-by-side construction of the treatment apparatus 10 of the present invention. As illustrated therein, plural columns 20 of contact surfaces 30 are provided, the columns being situated side-by-side in relation to one another. In the illustrated embodiment, there are five columns 20 of contact surfaces, although it should be understood that any number of columns 20 may be selected to form the desired width of the treatment apparatus 10. In this description, the term "contact surfaces" 30 is used interchangeably with "contact elements" and refer to the protruding elements in the treatment apparatus. In the illustrated embodiment, there are six contact surfaces 30 in each column 20, although it should be understood that any number of contact surfaces may be used to provide the desired height, as well as the desired therapeutic effect or size of treatment area. Each contact element 30 preferably has an undulating shape, with two peaks 35, 35 spaced apart and separated by a curved valley portion 38. The external slopes 39 of the contact elements 30, preferably also are sloped. However, it should be understood that any shaped contact element 30 may be used that can achieve the desired effect, such as flat top, triangular, double pointed peaks separated by a valley (rounded or angular), single rounded peak, single pointed peak, triple rounded peaks with two separating valleys (rounded or angular), triple pointed peaks separated by two valleys (rounded or angular), quadruple rounded peaks with four separating valleys (rounded or angular), quadruple pointed peaks separated by three valleys (rounded or angular), etc. The side surfaces 39 may be sloped or vertical as desired. Likewise, the top surface 37 of each peak 35 may have any desired profile. In the embodiment illustrated in FIGS. 6, 7, 12 and 13 the peak top surface 37 has a generally flat profile. However, it may also be curved, pointed or undulating or any other desired profile shape. The portion of the apparatus containing the contact surfaces will be referred to as the "operational portion" or "operational unit" herein.

FIGS. 9-16 illustrate another preferred construction of the treatment apparatus 10 of the present invention. In this construction, an operational unit 15 of a single column 20 of contact surfaces 30 is provided. In one embodiment there are forty-two contact surfaces 30 in the single column 20, although it should be understood that any number of contact surfaces 30 may be used to produce the desired length and therapeutic contact area for the treatment apparatus 10.

The contact surfaces 30 are positioned on a backplane 40 of the treatment apparatus 10, such as shown in the illustrated embodiments. The term "backplane" is used interchangeably herein with "mounting structure" to refer to the portion of the therapeutic apparatus 10 upon which the mounting surfaces 30 are situated. The contact surfaces 30 optionally may be mounted to the backplane 40 or may be integrally formed with it. If the contact surfaces 30 are mounted to the backplane 40, any suitable mounting material may be used that is of sufficient strength to attach the surfaces 30 to the backplane 40, such as mechanical fasteners such as rivets or screws, mating projections and apertures, or adhesives such as glue, wax or any other adhesive material.

In one example of the present invention, a plurality of contact elements are positioned on a mounting structure. Preferably the contact elements are integrally formed with the mounting structure, such as via a molding process or injection molding process. In addition, the device preferably is formed of a flexible material, such as a molded polymer or other flexible material. In this way, flexing can assist with maximizing the contact with the wearer, such as by contouring to the shape of the wearer's body and thereby enhancing the surface area that comes into contact with the wearer.

In one preferred example, each contact element is 4 cm. wide, has at least one peak that is 6 mm. high (i.e. extends from the mounting structure 6 mm.) and preferably two such peaks, although more may be used as well, and the contact element is 3 mm. high between peaks, in a multi-peak embodiment. Of course, any other dimensions and shape of contact element can be provided so long as contact elements can be arranged to provide contact or proximity to the wearer.

In an example of the embodiment illustrated in FIGS. 1-8, the operational unit is 10 cm. wide, 22 cm. long, and includes 30 concave ribs (i.e. contact elements) arranged in 5 columns each having 6 concave ribs. Of course other sizes and numbers of ribs may be used. For example if a larger coverage area is desired, each column may be lengthened, or alternatively, one or more columns may be added, or alternatively both longer columns may be used and one or more columns may be added.

In an example of the embodiment illustrated in FIGS. 9-16, the operational unit is 4 cm. wide, 66 cm. long, and includes 42 concave ribs (i.e. contact elements) arranged in a single column. Of course other sizes and numbers of ribs may be used.

In another example of the present invention, the operational unit is made of a PVC material, such as a medical use approved PVC compound. Of course, any other suitable material may be used, such as other polymeric materials or other moldable materials.

Figure 8:
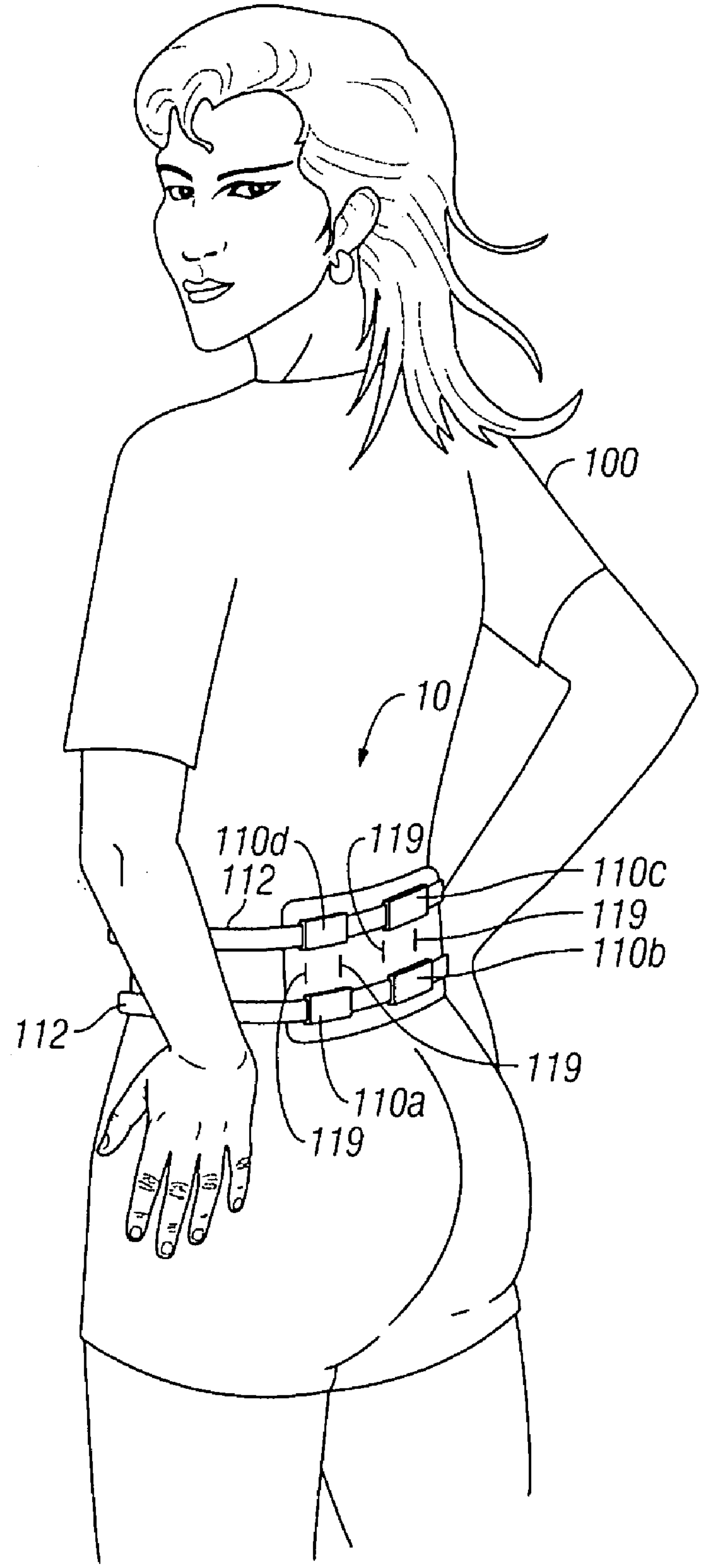
FIG. 8 is a view of a method of using an embodiment of the therapeutic treatment apparatus in accordance with the present invention.
Figure 16:
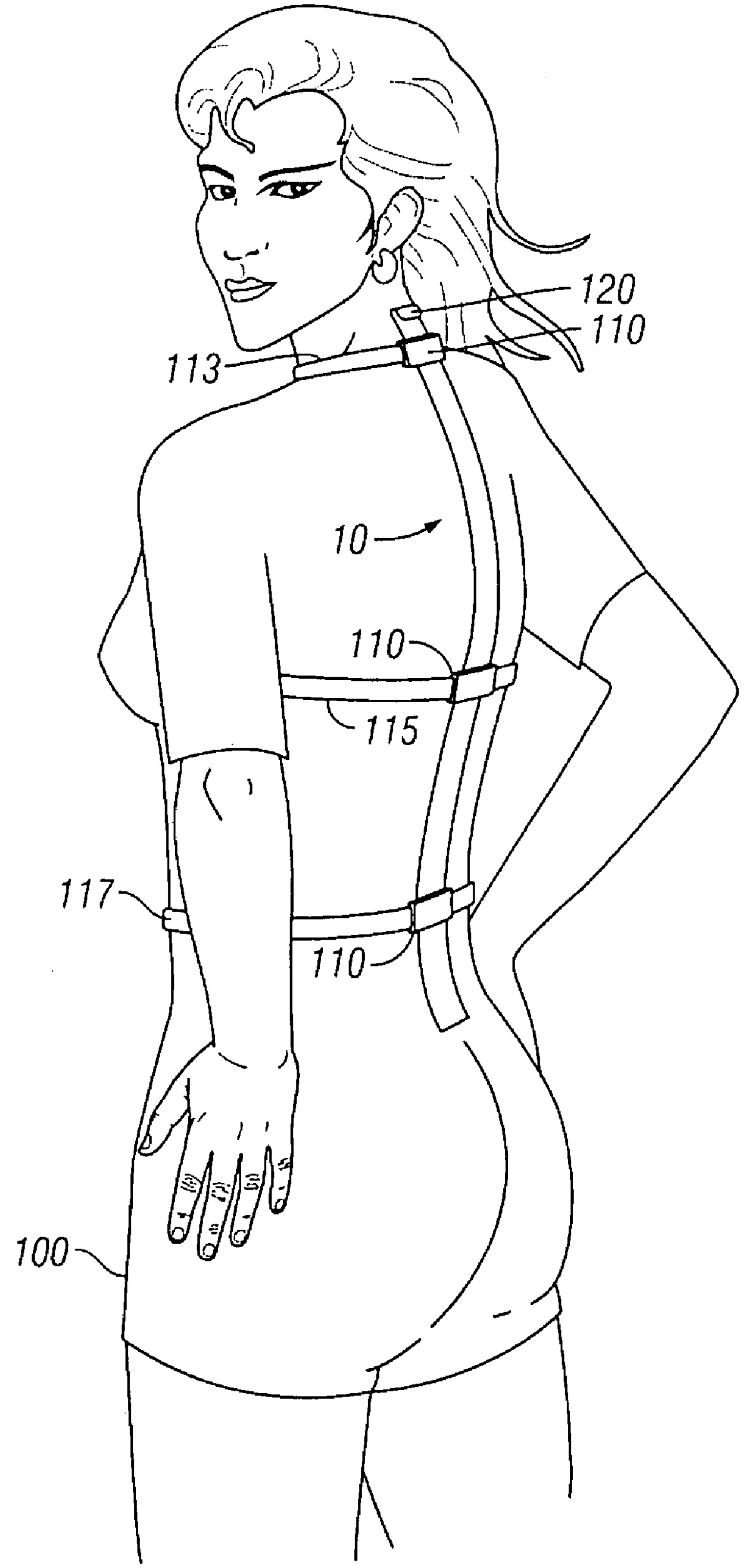
FIG. 16 is a view of a method of using an embodiment of the therapeutic treatment apparatus in accordance with the present invention.

Optional straps and mounting elements also are provided in an embodiment of the invention. These straps and mounting elements are used to attach the operational portion of the therapeutic apparatus 10 to a user. Two examples of a user 100 wearing the therapeutic apparatus 10 are illustrated in FIGS. 8 and 16.

Figure 9:
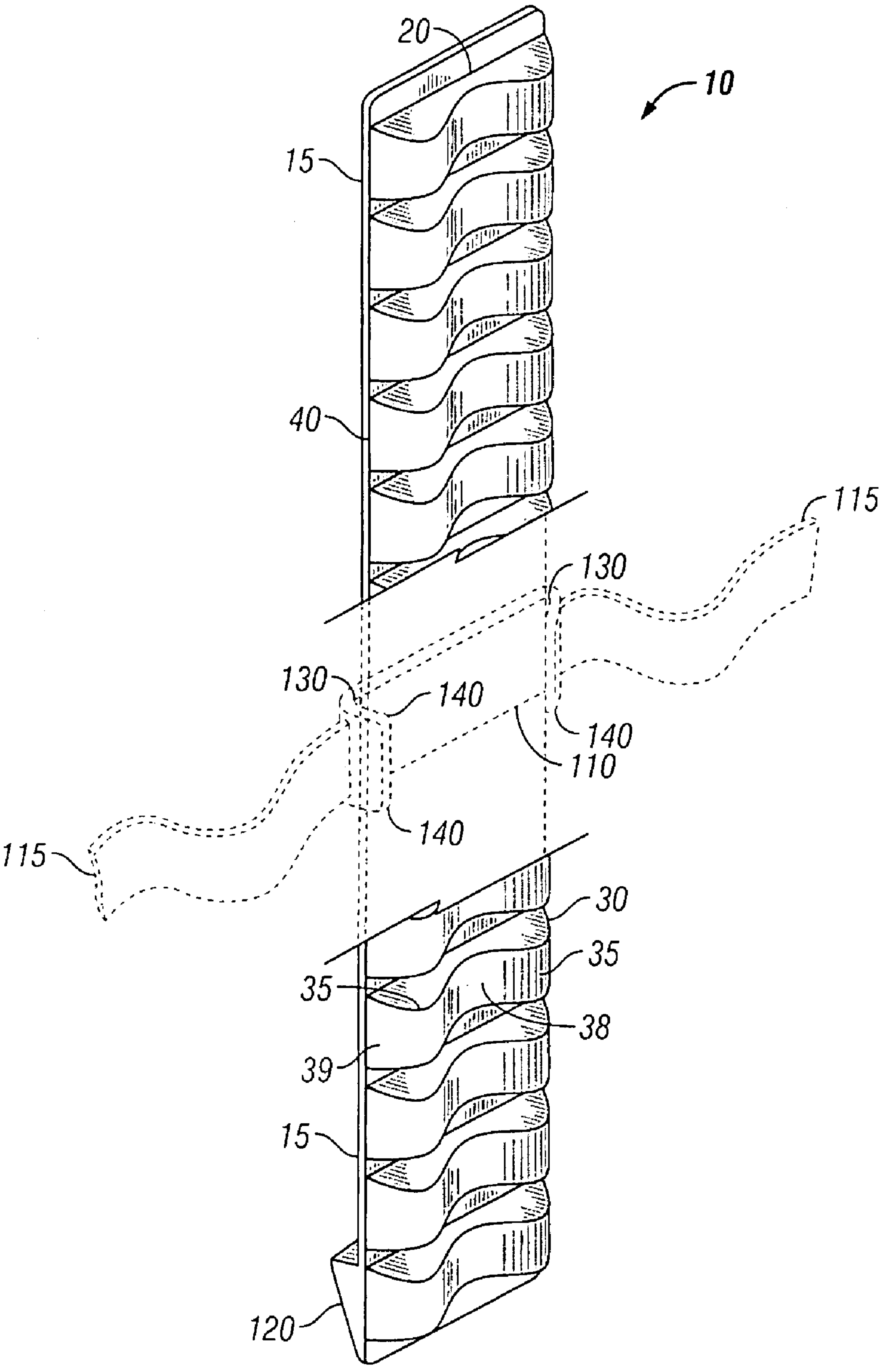
FIG. 9 illustrates a perspective view of a single-column embodiment of the therapeutic treatment apparatus in accordance with the present invention.
Figure 10:
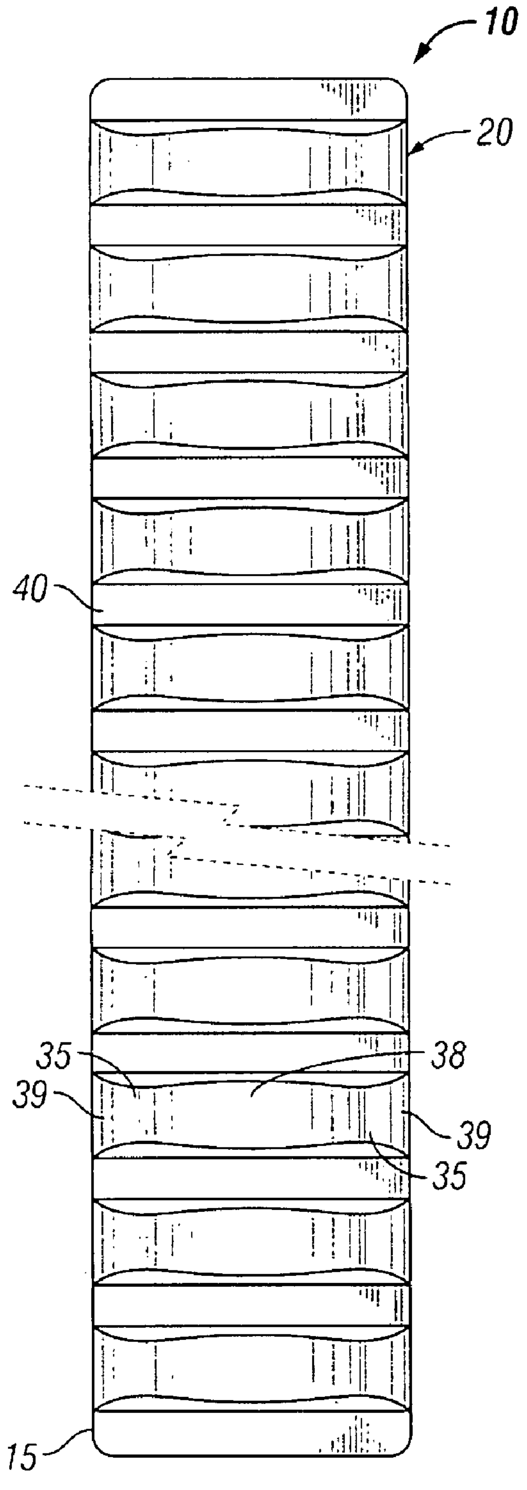
FIG. 10 illustrates a front view of a single-column embodiment of the therapeutic treatment apparatus in accordance with the present invention.
Figure 11:
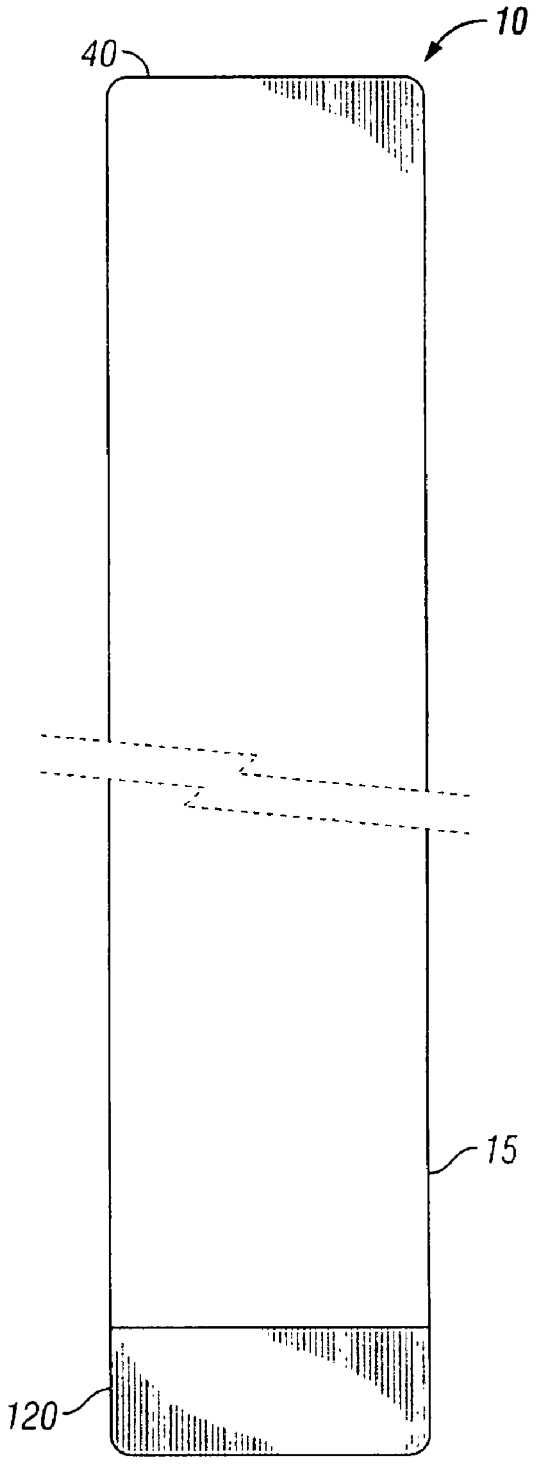
FIG. 11 illustrates a back view of a single-column embodiment of the therapeutic treatment apparatus in accordance with the present invention.
Figure 14:
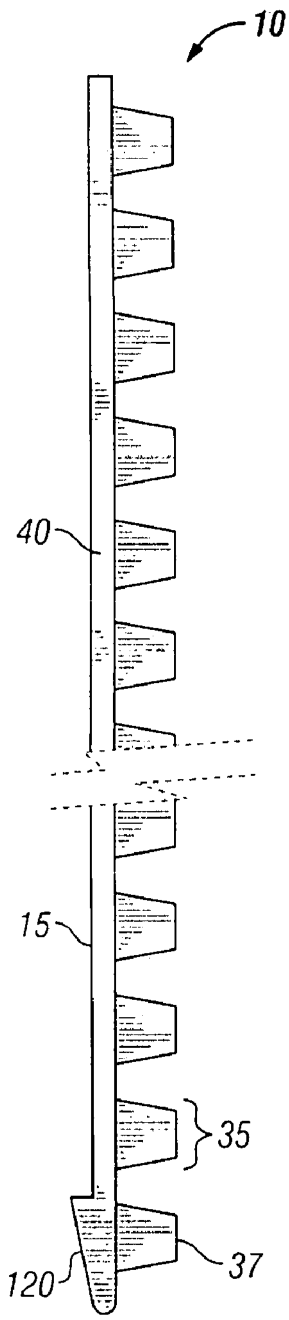
FIG. 14 illustrates a first side view of a single-column embodiment of the therapeutic treatment apparatus in accordance with the present invention.
Figure 12:
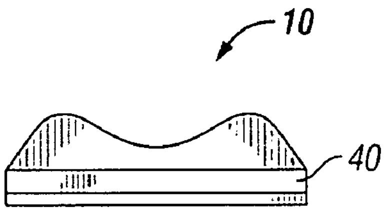
FIG. 12 illustrates a top view of a single-column embodiment of the therapeutic treatment apparatus in accordance with the present invention.
Figure 13:
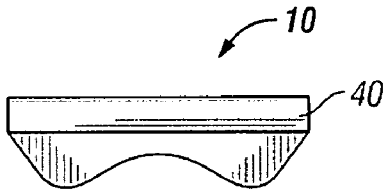
FIG. 13 illustrates a bottom view of a single-column embodiment of the therapeutic treatment apparatus in accordance with the present invention.
Figure 15:
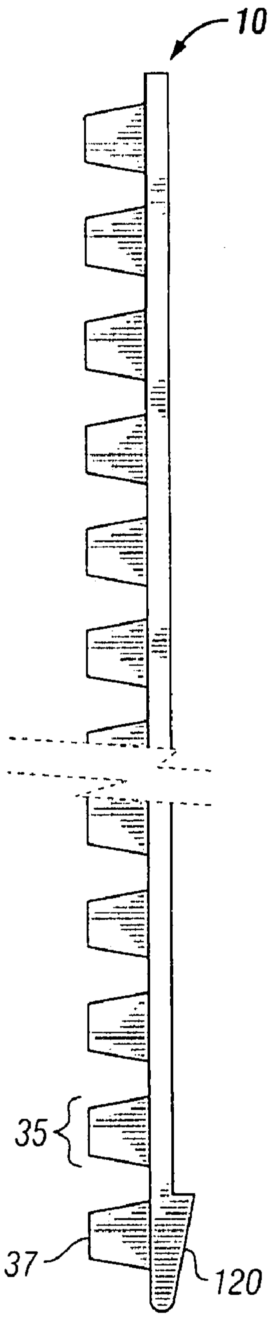
FIG. 15 illustrates a second side view of a single-column embodiment of the therapeutic treatment apparatus in accordance with the present invention.

In the embodiment illustrated in FIGS. 9-16, slidable mounting brackets 110 are provided. The mounting brackets 110 engage the long operational unit 15 of the therapeutic apparatus 10, as illustrated in FIGS. 9 and **17*f*. The brackets 110 can slide up and down the operational unit in any fashion desired by the user 100. In this embodiment, a projection 120 is provided at one end of the column 20. In another embodiment, projections 120 are provided at both ends. The projection(s) 120 serve to prevent any of the slidable mounting brackets 110 from slipping off the end(s). In a preferred embodiment of operation of the invention, a first mounting bracket 110 is positioned near the neck of user 100, a second is mid-way down the column 20 of the operational unit 15 and a third mounting bracket 110 is positioned in the vicinity of the lower back or waist. This arrangement is believed suitable for mounting the device 10 to the user 100**, along the user's spinal column, in a comfortable and secure fashion, although other arrangements also can be used.

In one embodiment, the mounting bracket 110 is curved at bends 130 to approximate the angle of side walls 39 with the backplane 40. In this way the mounting bracket 110 securely fits on the apparatus 10. Preferably the mounting brackets also have curved edges 140 so as to reduce the possibility of snagging or user discomfort. Such a rounded and matching shape is desired to enhance the ability of the mounting brackets 110 to slide easily for positioning along the operational unit 15 of the apparatus 10.

Figure 17A:
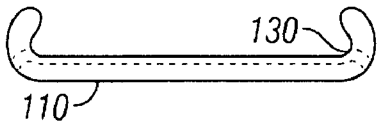
FIG. 17*a* illustrates a top end view of a mounting bracket in accordance with the present invention.
Figure 17B:
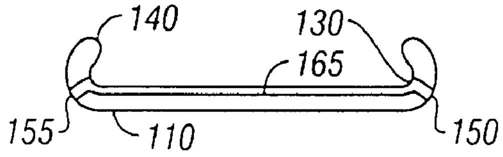
FIG. 17*b* illustrates a cross-sectional top end view of a mounting bracket in accordance with the present invention, taken along line b-b of FIG. 17*e;*
Figure 17C:
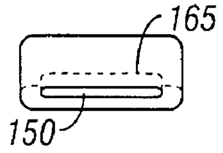
FIG. 17*c* illustrates a first end view of a mounting bracket in accordance with the present invention.
Figure 17D:
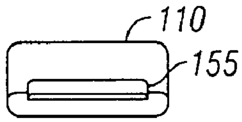
FIG. 17*d* illustrates a second end view of a mounting bracket in accordance with the present invention.
Figure 17E:
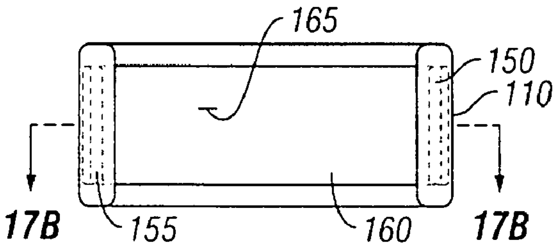
FIG. 17*e* illustrates a front view of a mounting bracket in accordance with the present invention.
Figure 17F:
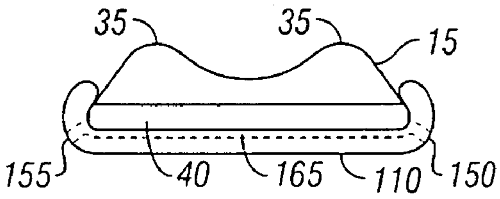
FIG. 17*f* illustrates a top end view of a mounting bracket and therapeutic treatment apparatus in accordance with the present invention.
Figure 18A:
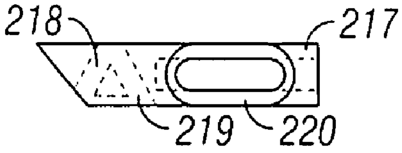
FIGS. 18*a-h* illustrate a buckle and binder system in accordance with the present invention.
Figure 18B:
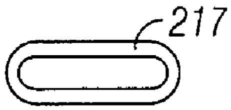
Figure 18C:
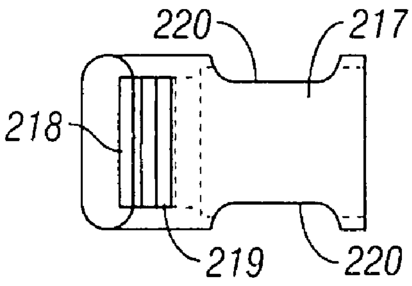
Figure 18D:
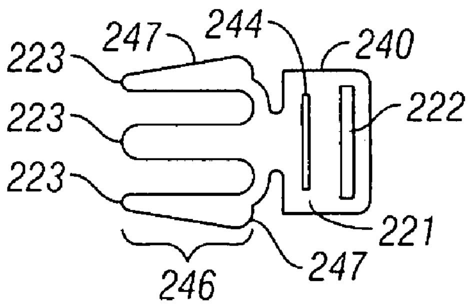
Figure 18E:
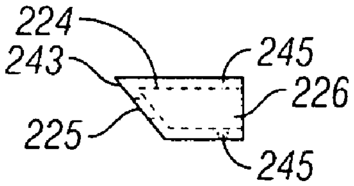
Figure 18F:
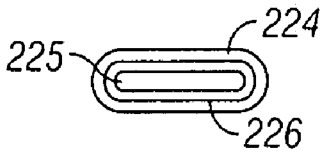
Figure 18G:
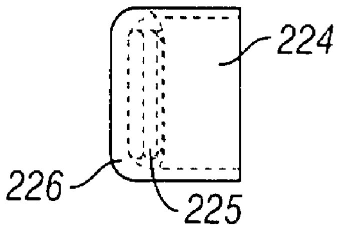
Figure 18H:
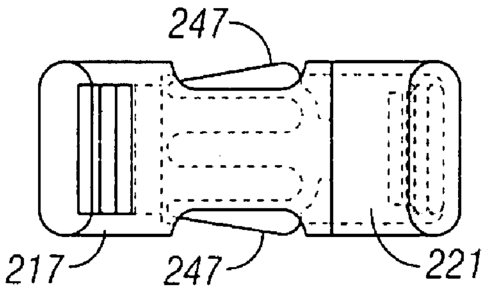

FIGS. **17*a* and 17*b* show respective side and side cross-sectional views of a mounting bracket 110. FIG. 17*b* is a cross-sectional view taken along line b-b shown in FIG. 17*e*. FIGS. 17*c* and 17*d* show respective end side views. FIG. 17*e* shows a front face view. FIG. 17*f* shows a side view of a mounting bracket 110 positioned on an operational unit 15 of a single column embodiment of the treatment apparatus 10. The mounting bracket includes side apertures 150, 155. The interior surface 160 of the mounting bracket optionally may include a groove 165 running the length from side aperture 150 to side aperture 155. A strap can be drawn through the side apertures 150,155 and along the groove 165**.

FIG. 16 illustrates one option for applying the treatment apparatus 10 to the back of a wearer 100. In the illustrated embodiment, the apparatus 10 is positioned along the spine so as to position the contact elements 30 adjacent the users spine. Preferably the operational portion of the apparatus is as long as the spine, although other lengths may be selected, such as shorter or longer. In the illustration, straps 113, 115 and 117 are mounted to the operational unit 15 of the apparatus 10 using mounting brackets 110 that are positioned along the apparatus. One or more slidable mounting brackets 110 optionally may be used, and preferably stops 120 are situated at one or both ends of the treatment apparatus 10. As with the other illustrated embodiment, the contact elements 30 are positioned on the inside, i.e. skin or clothing side. Optionally the wearer may apply the apparatus directly to the skin, or alternatively may have a barrier, such as clothing between the apparatus and skin.

A method of using the apparatus 10 by applying straps will now be described. Examples of buckles and strap binders that can be used with straps 112, 113, 115 and 117 are illustrated in FIGS. **18*a-h*, 19*a-h*, 20 and 21**. The straps preferably are elasticized so as to be stretchable, although non-stretch straps can be used as well.

One binder is illustrated in FIGS. **19*a-h*. This binder preferably is used in conjunction with straps 113 and 115, although it can be used with any of the straps 113, 115 or 117. In one embodiment, one end of strap 113 is bound, using a binder in accordance with the invention, in a substantially fixed and adjustable relation to a corresponding end of strap 115, strap 113 going over the user's shoulder and down in front, and strap 115 going under the user's arm and up in front. They are adjustably bound together using the binder, as described herein, although they can be tied, buckled or fastened in any fashion that secures them in place. The binder is used where it is desired to link together two strap end portions in an adjustable fashion. One end portion of a strap, such as an end of strap 113 is passed through and affixed to the binder. Another strap end, such as an end of strap 115 is drawn through in a slidably adjustable fashion. Alternatively two ends of the same strap can be bound together, although the example discussed herein will be an end of strap 113 and an end of strap 115**.

Figure 19A:
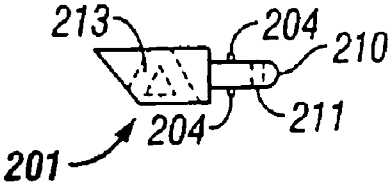
FIGS. 19*a-h* illustrate a binder system in accordance with the present invention.
Figure 19B:
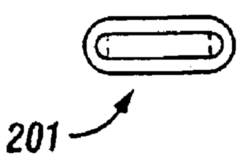
Figure 19C:
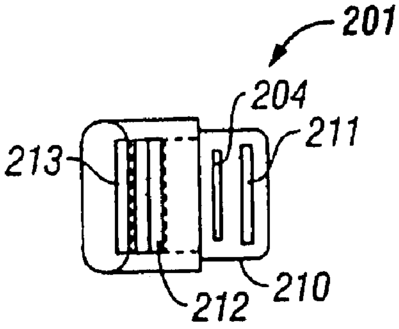
Figure 19D:
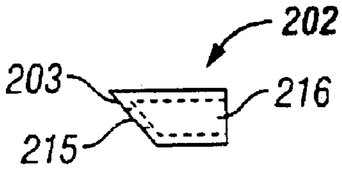
Figure 19E:
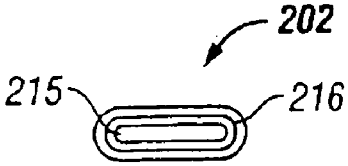
Figure 19F:
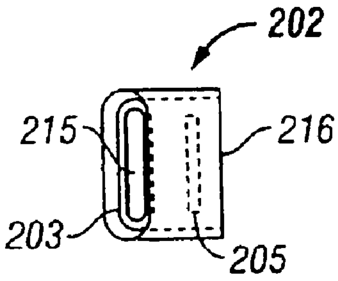
Figure 19G:
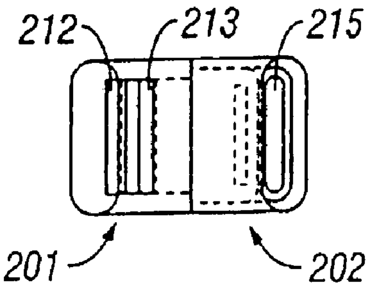
Figure 19H:
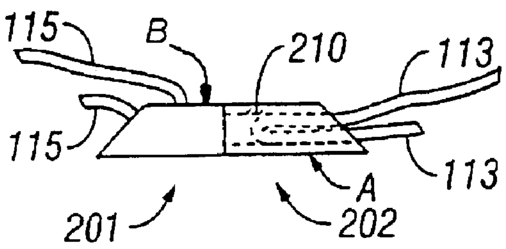
Figure 21:
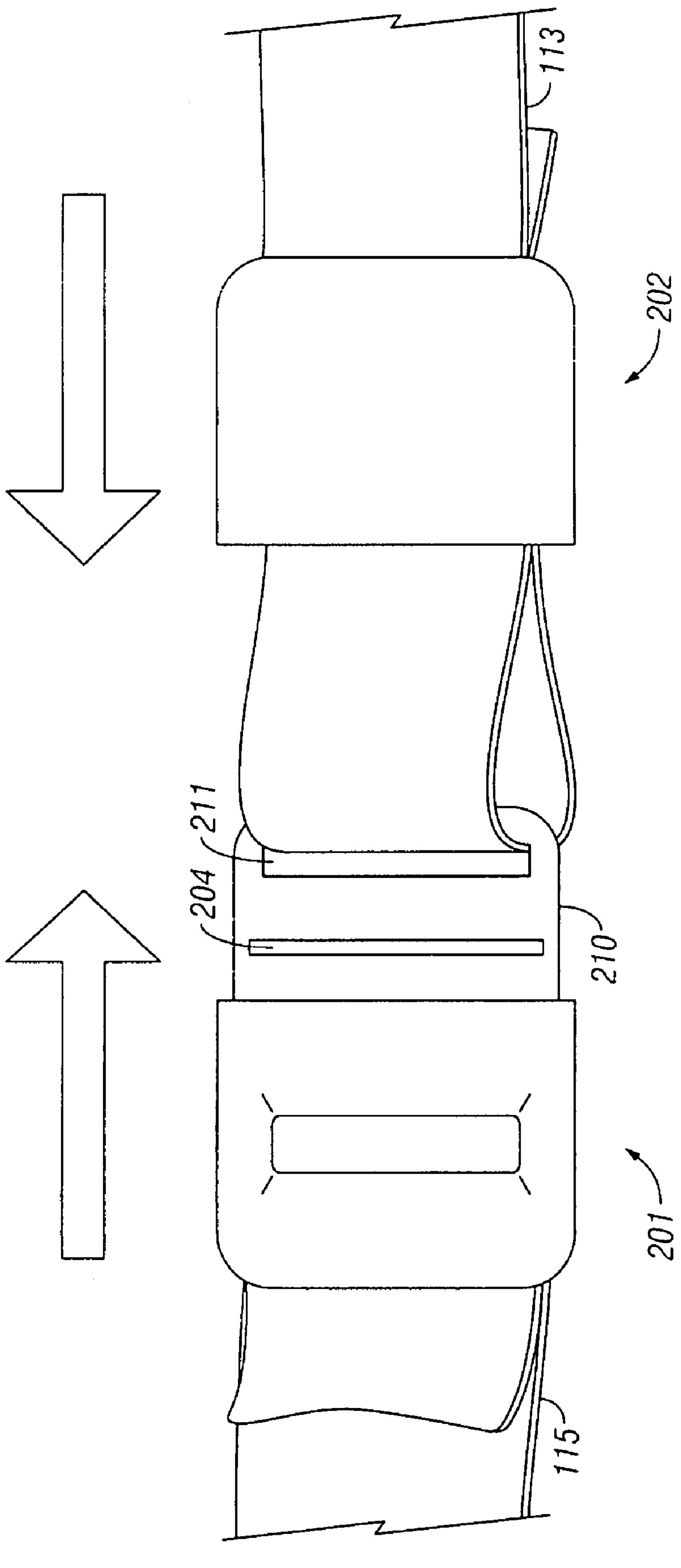
FIG. 21 illustrates a process of using a binder system in accordance with the present invention.

The binder includes two mating portions, insertion portion 201 and a receiving portion 202. The fixed strap end (such as an end of strap 113) is drawn through respective apertures defined in each of the insertion and receiving portions 201,

202, and then the insertion portion 201 is mated with the receiving portion 202 forming a secure connection and binding the strap in place. In operation, the fixed strap end is drawn first through the aperture 215 of binder receiving portion 202, all the way through the other end and out aperture 216. The aperture 215 preferably is positioned in a face 203 of the receiving portion 202, which is angled, facilitating insertion of the strap into aperture 215. The second aperture 216 of the binder receiving portion 202 optionally is wider than the first aperture 215. Then the strap is drawn through the aperture 211 of the insertion portion 201 and then back again through the aperture 216 of the receiving portion 202 and out aperture 215. The insertion portion 201 then is slid into receiving portion 202, securing the strap in place. As illustrated, the insertion portion 201 preferably includes and extension portion 210, that is dimensioned so as to fit into the aperture 216 of receiving portion 202 along with the strap. In use, the insertion portion is inserted until all of the extension portion 210 is inserted within receiving portion 202. This insertion process is illustrated in FIG. 21 in which the arrows show the directions of relative movement between the portions 201 and 202. In an embodiment, projections and indentations are provided that serve to lock in place the two portions 201, 202. For example, the insertion portion 201 can include projections 204 that are received in indentations 205 of receiving portion 202. To complete the connection of the strap ends, the end of strap 115 can be threaded though apertures 212 and 213 of the insertion portion 201 to a desired length. Preferably the binder is applied so that the angled side (side B, as illustrated in FIG. 19*h*) is adjacent the body of the user for greater comfort. In such an orientation, the straps exiting the binder (115, 113 as illustrated in FIG. 19*h*) fit into the binder and provide a softer contact. In addition, although the surfaces are shown to be angled, they can be squared or curved; an angled or trapezoid-like surface is understood to fit better into potential skin folds of a user minimizing discomfort. Thus, we have discussed linking of one end of strap 113 with one end of strap 115 around the shoulder of a user, using the binder described. The other ends of the same straps also may be bound together over/under the user's other shoulder using another one of the binders.

Another example of a suitable buckle/binder combination is now described with reference to strap 117 and FIGS. 18*a-h*. In this embodiment, the two strap ends of the same strap are connected to one another via the buckle/binder described. The buckle/binder includes three pieces, binder receiving part 224, binder insertion part 221 and buckle plug part 217. In operation, one end of the strap 117 can be threaded through apertures 150, and 155 of the mounting bracket 110. The other end of strap 117 is led first through a aperture 225 of the binder receiving portion 224, all the way through the other end and out aperture 226. The binder receiving portion 224 is similar to the receiving portion 202 discussed above. The aperture 225 preferably is positioned in a face 243 of the binder receiving portion 224, which is angled, facilitating insertion of the strap into aperture 225. The second aperture 226 of the binder receiving portion 224 optionally is wider than the first aperture 225. Then the strap is drawn through aperture 222 of the binder insertion part 221 and then back again through the aperture 226 of the binder receiving part 224 and out aperture 225. The insertion part 221 is then slid into aperture 226 of the receiving part 224, securing the strap in place. As illustrated, the insertion part 221 preferably includes an extension portion 240, that is dimensioned so as to fit into the aperture 226 of the receiving part 224, along with the strap. The insertion part 221 is inserted preferably until all of the extension portion 240 is inserted within the receiving part 224. In an embodiment, projections and indentations are provided that serve to lock in place the two parts 224, 221. For example, the insertion part 221 can include projections 244 that are received in indentations 245 of receiving part 224.

Figure 20:
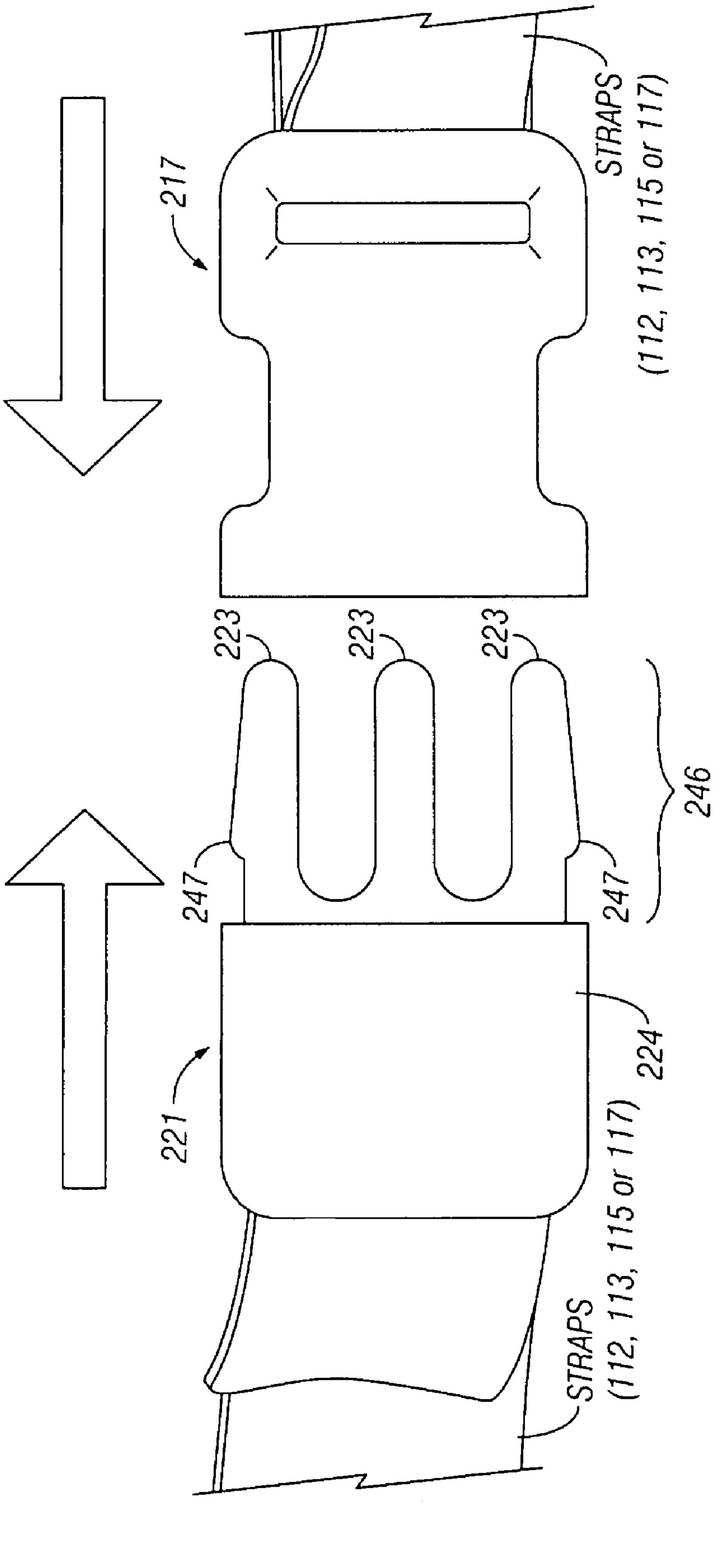
FIG. 20 illustrates use of a buckle system in accordance with the present invention.

The binder insertion part also includes a buckle insertion portion 246. Of course any type of buckle can be used that will be suitable for positioning and retaining in place the strap ends. In the illustrated embodiment, a triple-pole plug is provided, the buckle insertion portion 246 including three poles 223. The buckle plug part 217 of the has side apertures 220 into which edges 247 of the outermost poles 223 are received. The middle pole 223 of the buckle insertion portion 246 generally is straight, while the two outermost poles 223 have edges 247 with a curvature to enable the snap-in action when the buckle insertion portion 246 is inserted into the buckle plug part 217 and the edges snap-fit with the apertures 220. The side poles are pliant and are set apart adequately, so as to enable a snap-in action when inserted into the apertures 220 to fasten the strap 117 around the waist of the wearer 110 of the apparatus 10. The triple-pole plug 223 of the waist bracket is designed to open automatically when the force in the strap 117 exceeds certain value. This is a warning to the wearer that the length of the strap 117 has to be adjusted to enable comfortable wearing of the apparatus. This buckle insertion process is illustrated in FIG. 20 in which the arrows show the directions of relative movement between the portions 217 and 221.

Use of the straps and buckles now will be discussed with reference to FIG. 8, which illustrates one option for applying the treatment apparatus 10, such as to the lower back area of a wearer. In the illustration, a strap 112 is mounted to the apparatus using mounting brackets 110 (i.e. 110*a*, 110*b*, 110*c* and 110*d*) that are positioned in optional mounting bracket apertures 119 formed in the apparatus 10, such as in the backplane 40. The illustrated mounting brackets 110*a-d* can be affixed to the apparatus 10, using two of the apertures 119. The two ends of each of the mounting brackets 110*a-d* are pushed through respective apertures 119. Then a strap can be threaded through the bracket 110 (such as through its apertures 150, 155 and along the groove 165 of interior surface 160) thereby securing the strap to the apparatus 10. The strap can then be used to mount the apparatus 10 to the user. The contact elements 30 are positioned on the inside, i.e. skin or clothing side. Optionally the wearer may apply the apparatus directly to the skin, or alternatively may have a barrier, such as clothing between the apparatus and skin.

In the illustrated embodiment, in order to secure the strap 112 to the apparatus 10, four mounting brackets 110 (110*a* through 110*d*) are provided, using corresponding four pairs of apertures 119 for mounting on the apparatus 10. The strap 112 is drawn through the side apertures of the mounting brackets 110*a* and 110*b* and then through the binder 224 of a buckle, then through the aperture 222 of the plug part 221 of the waist bracket and back through the binder 224 and then back through the remaining mounting brackets 110*c* and 110*d*, such as through their respective side apertures 150, 155. The beginning and the end of the strap 112 are drawn together through the apertures 218 and 219 of the socket part 217 of the waist bracket. In use, it is desired to even out the loose ends of the strap 112, although they also may be uneven. When the strap is adjusted as desired, binder 224 is pushed onto the straight side of the plug part 221 of the waist bracket, thereby securing the strap in the buckle.

Figure 22:
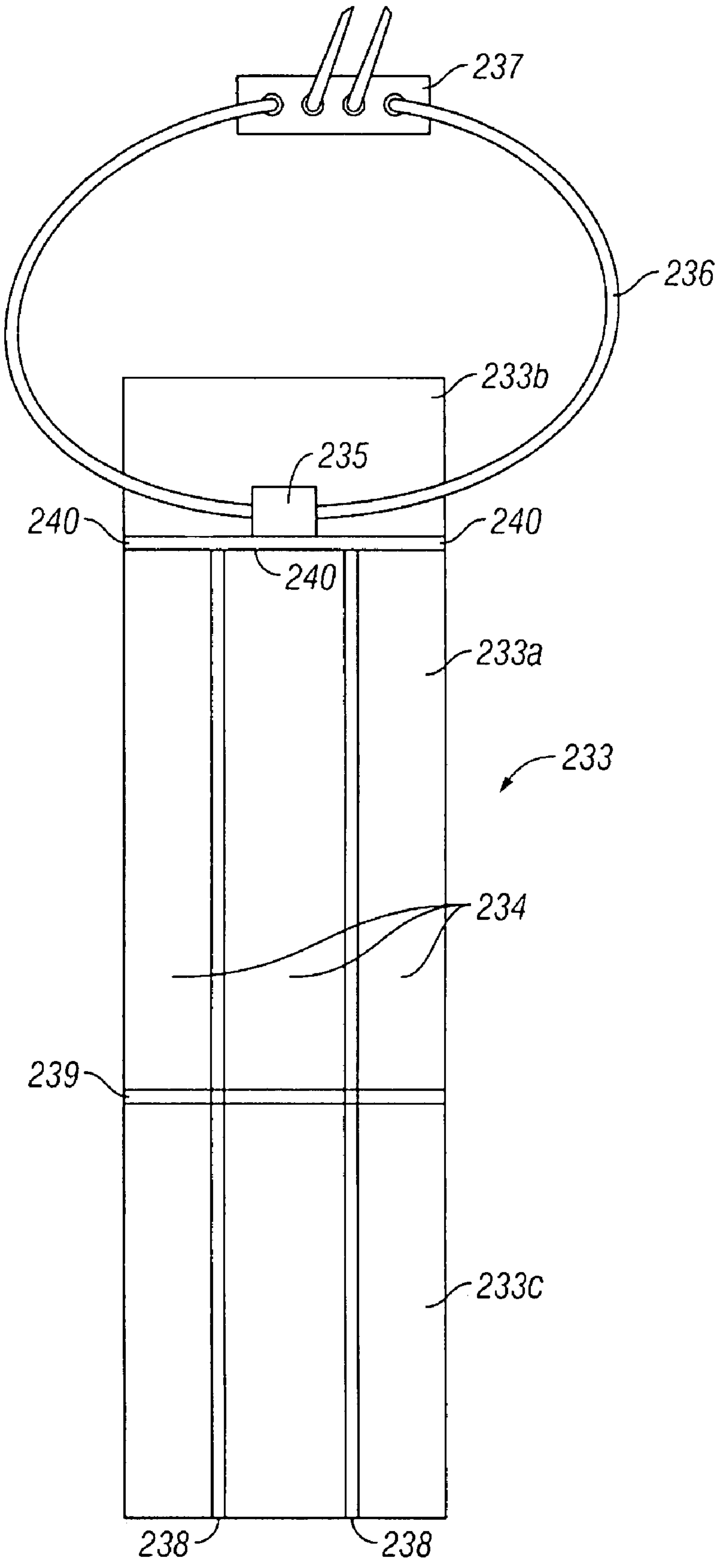
FIG. 22 illustrates a carrying bag system in accordance with the present invention.

In an alternative embodiment illustrated in FIG. 22, a carrying bag 233 is provided for mounting the therapeutic treatment apparatus 10. In one embodiment, the carrying bag 233 has one or more pockets 234 where one or more therapeutic treatment apparatus 10 are positioned. In the illustrated embodiment, three pockets 234 are provided. It should be recognized that any form of the apparatus may be used, such as the columnar version such as shown in FIG. 9 (of any desired length), or the multi-column version, such as shown in FIG. 1 (of any desired size as well). Any desired number of apparatus 10 also may be positioned within each of the pockets. In one example, columnar therapeutic treatment apparatus 10 (such as shown in FIG. 9) are used, each having 23 or 24 contact elements 30 positioned on them. Three such apparatus 10 are positioned in each of the pockets 234 of the carrying bag 233, making nine total. Of course other numbers, sizes and shapes may be selected. In this example, the upper part 233*b* of the carrying bag 233 takes approximately one sixth of the length and is sewn up at its sides, while the shorter side is not sewn up. The parts 233*a* and 233*c* of the carrying bag 233 have three vertical sections made by means of two parallel seams 238 extending in the lengthwise direction. At approximately two sixths of the length of the bag, a seam (or seams) 239 is provided across the width of the bag 233 to close completely the section 233*c*, and enclosing the apparatus 10 positioned within the enclosed pockets of it (if any). Optionally no apparatus 10 are positioned within section 233*c*. The apertures 240 for the therapeutic apparatus 10 allowing them to be positioned in (or removed from) the pockets in section 233*a* are on the upper side of the part 233*a*. Near the upper side of part 233*a*, and in the middle of part 233*b* an optional band 235 is sewn, through which a fastening cord 236 can be drawn. One end of the cord 236 is drawn through two apertures on one side of the buckle 237, while the other end of the cord 236 is drawn through two apertures on the other side of the buckle 237. The buckle 237 can be of any shape, but in the illustrated example is rectangular and has rounded edges; four apertures are arranged evenly along its length. Examples of uses for this embodiment, are for use in public places, where the therapeutic apparatus 10 is shielded, from view by the carrying case 233. In use, the apparatus is mounted on a user, such as on the user's back in such a way, that its lower end 233*b* is placed on the lower back and that by stretching the cord 236 the middle part of the bag 233*a*, with the therapeutic apparatus 10 is positioned such as in the middle of the user's back.

By positioning the therapeutic treatment apparatus on the back of a user, various advantages can be gained for the user. For example, and without limitation, a properly adjusted apparatus 10 according to the invention can promote the wearer to hold his/her back in a good position and improve posture. Doing so can promote good use of muscles thereby helping to reduce and/or eliminate back pain, if any. The contact elements 30 with their bulges also can have a massaging effect, that can enhance muscle and spinal comfort and assist with improved blood circulation in the massaged region. In an embodiment in which the apparatus 10 is positioned along the spine, the 35 can be positioned on respective sides of the spine, providing a massaging effect along the sides of the spinal column. In addition, placing the apparatus on a user's back, can warm the area of placement, with benefit to tissue, nerves muscles etc. in the affected area. Due to these various effects, a reduction in back pain has been observed in various users.

Thus, it is seen that a treatment apparatus and methods of using it are provided. One skilled in the art will appreciate that the present invention can be practiced by other than the preferred embodiments, which are presented in this description for purposes of illustration and not of limitation. It is noted that equivalents for the particular embodiments discussed in this description may practice the invention as well.

What is claimed is:

1. A therapeutic treatment apparatus comprising:

a unitary mounting structure having a first surface and a second surface opposite the first surface;

a plurality of contact elements on the first surface of the mounting structure and integrally formed with the mounting structure forming a unitary one-piece structure including the contact elements and the mounting structure, each element including a contact surface having at least one peak, each peak having a summit and sides extending therefrom;

the contact elements arranged in fixed position in a single column on the mounting structure; and a projection positioned on the second surface of the mounting structure.

2. The therapeutic treatment apparatus of claim 1 wherein the mounting structure has first and second ends and the projection is positioned at one or both of the first and second ends.

3. The therapeutic treatment apparatus of claim 2 further comprising a mounting bracket slidably positioned on the treatment apparatus, wherein the projection prevents the mounting bracket from slipping off one or both of the first and second ends of the therapeutic treatment apparatus.

4. The therapeutic treatment apparatus of claim 3 further comprising:

at least one strap attached to the treatment apparatus using the mounting bracket, each of the at least one strap including at least one strap end portion; and at least one securing apparatus attached to the strap allowing respective strap end portions to be secured in substantially fixed relation to one another.

5. The therapeutic treatment apparatus of claim 4 further comprising:

a second mounting bracket;

at least two said straps attached to the treatment apparatus using the first and second mounting brackets respectively and wherein each of said straps includes at least one strap end portion; and wherein the securing apparatus is attached to at least two said straps allowing one of the strap end portions of one said strap to be secured in substantially fixed relation to one of the strap end portions of another said strap.

6. The therapeutic treatment apparatus of claim 4 wherein the securing apparatus comprises a binder including:

an insertion portion; and a receiving portion.

7. The therapeutic treatment apparatus of claim 4 wherein the securing apparatus comprises a buckle apparatus including:

a buckle insertion portion including:

a binder receiving portion;

a binder insertion portion matable with the binder receiving portion; and a protruding buckle insertion member; and a buckle receiving portion mating with said protruding buckle insertion member.

8. The binder apparatus of claim 7 wherein said insertion portion further defines a second aperture in said insertion portion through which said second strap end portion can be drawn and a third aperture in said insertion portion through which said second strap end portion can be drawn after being drawn through the first aperture in said insertion portion.

9. The binder apparatus of claim 7 wherein said first strap end portion and said second strap end portion are on respective first and second straps.

10. The binder apparatus of claim 7 wherein said first strap end portion and said second strap end portion are on the opposite ends of a single strap.

11. The therapeutic treatment apparatus of claim 4 wherein:

the strap end portions include first and second strap end portions, each said strap end portion including a strap terminating at a terminal end; and the securing apparatus includes:

a binder receiving portion defining first and second apertures, a strap passable into the binder receiving portion via the first aperture and out of the binder receiving portion via the second aperture; and a binder insertion portion defining a third aperture that is sized such that the strap is passable through the third aperture, the binder insertion portion including a protruding insertion member dimensioned to fit within the binder receiving portion via said second aperture.

12. The therapeutic treatment apparatus of claim 4 wherein:

the strap end portions include first and second strap end portions, each said strap end portions including a strap terminating at a terminal end; and the securing apparatus includes:

a binder apparatus for securing a first strap end portion and a second strap end portion in substantially fixed and adjustable relation with one another, each said strap end portion including a strap terminating at a terminal end, the binder apparatus comprising:

a receiving portion including a first aperture of said receiving portion through which the first strap end portion can be drawn through into the receiving portion and a second aperture of said receiving portion through which the first strap end portion can be drawn through and out of the receiving portion;

an insertion portion matable with the receiving portion including an aperture in the insertion portion through which the first strap end portion can be drawn through and wherein said first strap end portion then can be drawn through said second aperture of said receiving portion and out through said first aperture of said receiving portion; and means for mating together the receiving portion and the insertion portion substantially securing said first strap end portion in place relative to said binder apparatus.

13. A method of adjustably securing a first strap end portion and a second strap end portion in substantially fixed and adjustable relation with one another using a binder apparatus including an insertion portion and a receiving portion matable with one another, each said strap end portion including a strap terminating at a terminal end, the method comprising:

drawing the first strap end portion in through a first aperture of said receiving portion and out through a second aperture of said receiving portion;

drawing the first strap end portion through an aperture in the insertion portion;

drawing the first strap end portion in through said second aperture of said receiving portion and out through said first aperture of said receiving portion;

mating together the receiving portion and the insertion portion substantially securing said first strap end portion in place relative to said binder apparatus;

drawing at least one of said first and second strap end portions through at least one strap retaining structure on a mounting bracket;

providing a therapeutic treatment apparatus; and slidably positioning said mounting bracket to the therapeutic treatment apparatus.

14. A strap binder apparatus comprising:

a binder receiving portion defining first and second apertures, a strap passable into the binder receiving portion via the first aperture and out of the binder receiving portion via the second aperture, wherein a surface of the binder receiving portion at which the first aperture is located is angled relative to a longitudinal axis of the first aperture; and a binder insertion portion defining a third aperture, a strap passable through the third aperture, the binder insertion portion including:

a protruding insertion member dimensioned to fit within the binder receiving portion via said second aperture.

15. The strap binder apparatus of claim 14 wherein the binder insertion portion defines fourth and fifth apertures adapted to adjustably securing a second strap.

16. A therapeutic treatment apparatus comprising:

a mounting structure having first and second ends and a first surface and a second surface opposite the first surface;

a plurality of contact elements on the first surface of the mounting structure, each element including a contact surface having at least one peak, each peak having a summit and sides extending therefrom;

the contact elements arranged in fixed position in a single column on the mounting structure;

a projection positioned on the second surface of the mounting structure at one or both of the first and second ends; and a mounting bracket slidably positioned on the treatment apparatus, wherein the projection prevents the mounting bracket from slipping off one or both of the first and second ends of the therapeutic treatment apparatus.

17. The therapeutic treatment apparatus of claim 16 further comprising:

at least one strap attached to the treatment apparatus using the mounting bracket, each of the at least one strap including at least one strap end portion; and at least one securing apparatus attached to the strap allowing respective strap end portions to be secured in substantially fixed relation to one another.

18. The therapeutic treatment apparatus of claim 17 further comprising:

a second mounting bracket;

at least two said straps attached to the treatment apparatus using the first and second mounting brackets respectively and wherein each of said straps includes at least one strap end portion; and wherein the securing apparatus is attached to at least two said straps allowing one of the strap end portions of one said strap to be secured in substantially fixed relation to one of the strap end portions of another said strap.

19. The therapeutic treatment apparatus of claim 17 wherein the securing apparatus comprises a binder including:

an insertion portion; and a receiving portion.

20. The therapeutic treatment apparatus of claim 17 wherein the securing apparatus comprises a buckle apparatus including:

a buckle insertion portion including:

a binder receiving portion;

a binder insertion portion matable with the binder receiving portion; and a protruding buckle insertion member; and a buckle receiving portion mating with said protruding buckle insertion member.

* * * * *